United States Patent [19]

Still et al.

[11] Patent Number: 4,496,751

[45] Date of Patent: Jan. 29, 1985

[54] DIFUNCTIONAL FURAN DERIVATIVES

[75] Inventors: Richard H. Still, Disley; John L. Cawse, Manchester; John L. Stanford, Flixton, all of England

[73] Assignee: The University of Manchester Institute of Science & Technology, Manchester, England

[21] Appl. No.: 481,370

[22] Filed: Apr. 1, 1983

[51] Int. Cl.³ .................. C07D 307/52; C07D 307/66
[52] U.S. Cl. ...................................... 549/472; 528/73; 548/122; 549/473
[58] Field of Search ............................... 549/472, 473; 260/453 P

[56] References Cited

U.S. PATENT DOCUMENTS 2,681,917 6/1954 Fauqué ................................ 549/472
3,268,542 8/1966 Burk et al. ........................ 260/453 P
3,725,450 4/1973 Cowry et al. ..................... 260/453 P

FOREIGN PATENT DOCUMENTS 588377 5/1947 United Kingdom .
190906 3/1967 U.S.S.R. .

Primary Examiner—Richard L. Raymond
Attorney, Agent, or Firm—Pravel, Gambrell, Hewitt & Kimball

[57] ABSTRACT

Compounds of the formula (I)

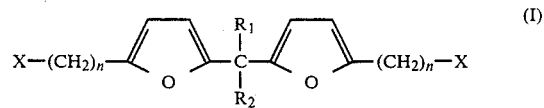

in which $R_1$ and $R_2$ are the same or different and are selected from hydrogen, substituted or unsubstituted methyl or ethyl radicals, and substituted or unsubstituted vinyl radicals, X is a —$NH_2$ or —NCO group, and n is 0 or 1 with the proviso that n is not 0 when X is —$NH_2$.

10 Claims, No Drawings

DIFUNCTIONAL FURAN DERIVATIVES

This invention relates to difunctional furan derivatives.

The polyfunctional isocyanates and polyfunctional amines as used respectively for the manufacture of polyurethanes and polyamides are frequently derived from oil-based products. For example, diphenylmethane diisocyanate (MDI), which is one of the most commonly used isocyanates for polyurethane formation, is produced from aniline, itself derived from oil.

Whilst the polyfunctional amines and isocyanates obtained from oil-based feedstocks are satisfactory for manufacturing polyurethanes and polyamides the fact that they are derived from oil is making them increasingly expensive. There is the additional disadvantage that oil stocks are dwindling so that replacements for the oil-derived isocyanates and amines will have to be found.

Any such replacements will be required to have at least some of the properties of the oil derived isocyanates and amines. With specific reference to polyurethane formation, MDI is important for its ability to confer improved properties in the finished polyurethane due, at least in part, to the linear rigid structure of the MDI molecule. Additionally MDI is normally used in its crude form in which it is a liquid, as compared to pure MDI which is a white solid. Crude MDI has the advantage of being of low volatility and hence low toxicity. Furthermore, crude MDI is eminently suitable in the production of polyurethanes by Reaction Injection Moulding (RIM) or Reinforced Reaction Injection Moulding (RRIM), these being processes in which two liquid reactant streams (i.e. isocyanate and polyol) are caused to impinge on each other at high velocity in a mixing head before passing to a mould. The usefulness of crude MDI in RIM and RRIM techniques stems, of course, from the fact that it is a liquid.

Any isocyanate produced as an alternative to the oil-derived MDI should have at least some of the properties discussed above.

The compounds of this invention proposed as alternatives to oil-derived isocyanates are defined below, and include inter alia diisocyanates and diamines based on the difuryl alkane skeleton. Although difuryl alkanes are known from the literature, isocyanate and amine derivates thereof have not been described.

Thus U.S. Pat. No. 2,681,917 describes difurylalkanes suitable for use in perfumery of the general formula

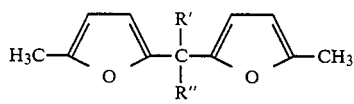

and Russian Pat. No. 190,906 describes difurylalkanes of general formula

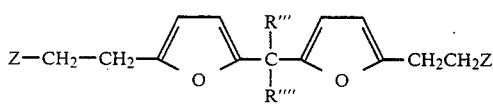

in which R''' and R'''' are H or CH$_3$ and Z is, for example, —CO$_2$Et, —CH$_2$CO$_2$Et.

According to a first aspect of the present invention we provide compounds of the formula (I)

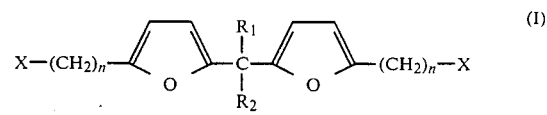

in which R$_1$ and R$_2$ are the same or different and are selected from hydrogen, substituted or unsubstituted methyl or ethyl radicals, and substituted or unsubstituted vinyl radicals, X is a —NH$_2$ or —NCO group, and n is 0 or 1 with the proviso that n is not 0 when X is —NH$_2$.

In the case where R$_1$ and/or R$_2$ are substituted methyl, ethyl or vinyl radicals, the substituent is preferably at least one halogen atom, e.g. Cl, Br or I. For example, a trichloromethyl group may be used as R$_1$ or R$_2$ or alternatively a group of formula Z$_2$C=CH— where Z is a halogen.

Specific compounds which are of particular interest within the scope of the invention are as follows:

X=—NCO 1. bis(5-isocyanato-2-furyl)methane
   (n=0; R$_1$=H; R$_2$=H)
2. 1,1-bis(5-isocyanato-2-furyl)ethane
   (n=0; R$_1$=Me; R$_2$=H)
3. bis(5-isocyanatomethyl-2-furyl)methane
   (n=1; R$_1$=H; R$_2$=H)
4. 1,1-bis(5-isocyanatomethyl-2-furyl)ethane
   (n=1; R$_1$=Me; R$_2$=H)
5. 2,2-bis(5-isocyanatomethyl-2-furyl)propane
   (n=1; R$_1$=Me; R$_2$=Me)

X=—NH$_2$ 6. bis(5-aminomethyl-2-furyl)methane
   (n=1; R$_1$=H; R$_2$=H)
7. 1,1-bis(5-aminomethyl-2-furyl)ethane
   (n=1; R$_1$=Me; R$_2$=H)
8. 2,2-bis(5-aminomethyl-2-furyl)propane
   (n=1; R$_1$=Me; R$_2$=Me)

The compounds of this invention are useful reagents for the preparation of polymers. Thus the reaction of one of the new diisocyanates with a polyfunctional hydroxy-compound (polyol) will result in the formation of a polyurethane. Depending on which diisocyanate is used and on the nature of the chosen polyol, polyurethanes may be produced having differing properties, for example rubbers, glasses or foamed structures may be formed. In a similar way, the new diamines may be converted into polymers by reaction with a suitable polyfunctional reagent, such as a diacid chloride or dicarboxylic acid, to form a polyamide.

The isocyanates of this invention are particularly attractive for use in a variety of industrial processes, including casting, low-pressure dispensing, and Reaction Injection Moulding (RIM), owing to their high reaction rates, low volatility and liquid nature. Especially suitable are compounds 3, 4 and 5 which have very faint odours, making them pleasant to work with and which are relatively stable under ambient conditions. These isocyanates do not readily form insoluble oligomers under normal circumstances, which is an advantage over some of the presently available isocyanates which are susceptible to dimer formation.

The reactivity of the amines and isocyanates of this invention in polymer forming reactions is similar to that of aromatic amines and isocyanates, this being due to the proximity of the amino or isocyanate groups to the furan nucleus.

The compounds of the present claim are of further interest in that they may all be derived from non-oil-based feedstocks, particularly from furfural as will be appreciated from the description given hereinbelow as to the manner in which the compounds may be prepared. Furfural is obtained easily from agricultural residues such as corn-cobs, sugar-beet pulp and bagasse, by distillation with dilute acid. The furfural may then be converted by simple and economical steps into the starting materials for preparing the compounds of the invention.

Formation of the difuryl alkane skeleton may be by condensation, preferably under acid conditions, of a 2-substituted furan derivative with a carbonyl compound of formula II.

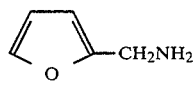

in which $R_1$ and $R_2$ are as defined above, or a compound which behaves as, or is converted to, a compound II under the reaction conditions, e.g. an acetal or vinyl ether, which are also referred to herein as compounds (II). The condensation reaction is generally conducted in the presence of a mineral acid and at a temperature of 0° to 40° C.

The 2-substituted furan starting material is selected depending on the value of n and identity of X in the desired compound (I). For $n=1$ and $X=-NH_2$ or $-NCO$ the starting compound may be furfurylamine (III) which is condensed either in free or protected form

with the compound (II), as detailed more fully below so that there may be obtained a compound of formula (Ia)

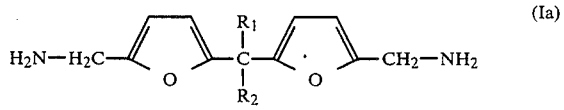

i.e. a compound of formula (I) with $n=1$ and $X=NH_2$. Compound (Ia) may then if desired by converted by known techniques e.g. phosgenation, to the diisocyanate (compound (I): $n=1$, $X=-NCO$). This route for preparing compounds (Ia) and the corresponding isocyanates is referred to below as Route A.

With regard to the production of compounds (Ib)

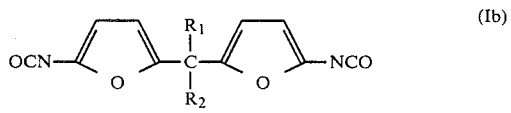

i.e. compounds I in which $n=0$ and $X=NCO$ it should be noted that they cannot be prepared by the conventional route of phosgenation of a diamine. This is due to the inherent instability of furylamines of general structure.

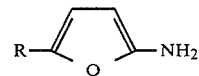

Compounds (Ib) can however be prepared by thermal rearrangement of either azides (IV) (Route B) with loss of nitrogen (i.e. Curtius Rearrangement).

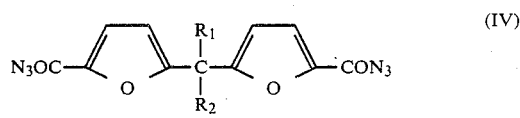

or nitrile sulphites (V) (Route C) with loss of $SO_2$

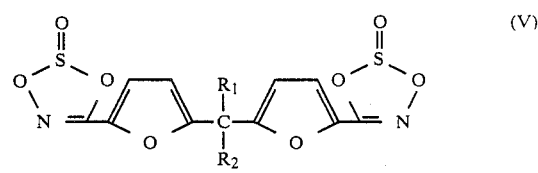

The preparation of azides (IV) and nitrile sulphites (V) is given below.

Further details will now be given as to the way in which Routes A–C may be effected.

ROUTE A

This route aims to produce the amines (Ia)

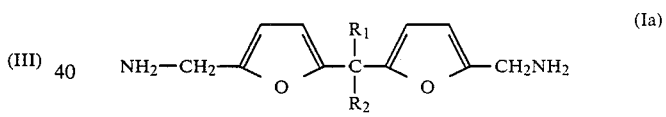

and isocyanates derived therefrom.

In this route, the difuryl skeleton is preferably formed by condensation of the amine III (which is readily derived from furfural) or a derivative thereof (e.g. the N-formamide derivative (NFF)) with a compound (II) in accordance with the following generalised reaction scheme

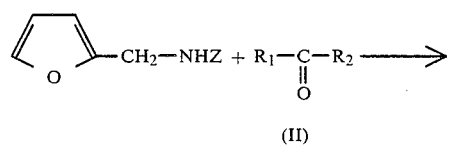

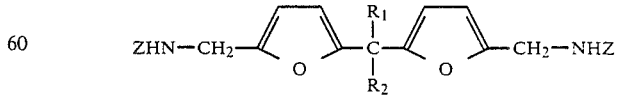

in which Z is hydrogen or a protecting group. Condensation is preferably effected in aqueous mineral acid such as hydrochloric acid or orthophosphoric acid at a temperature typically in the range of $-10°$ to 50° C. Generally an excess of 5 to 50% of compound (II) on the basis of stoichiometry is used. Reaction time is dependent particularly on the nature of compound (II); thus ketones require longer reaction times than aldehydes. The nature and concentration of the acid may also affect reaction time and yield: thus concentrated hydrochloric acid (ca 10M) is required for high conversion of NFF at a fast rate when compound (II) is acetone, unless longer reaction times are acceptable in which case the acid concentration may be reduced, e.g. to 3M.

The condensation product between NFF and compound (II) is a polyfunctional N-substituted formamide which may be readily hydrolysed under alkaline conditions to give an oligomeric polyfunctional amine consisting mainly of compound (Ia) which may if desired be obtained in pure state by fractional distillation under reduced pressure. Isocyanate of formula I in which X is NCO and n is 1 may be prepared by reaction of amines (Ia) or their hydrochlorides with phosgene in an inert solvent such as chlorobenzene. Crude isocyanate will be obtained by using the unpurified amine (Ia), and relatively pure diisocyanate by use of the pure amine. Crude isocyanate will be satisfactory for many uses so that purification of the amine (Ia) is not necessary.

As a modification to the use of NFF the free amine (III) may, in certain cases and under suitable conditions be condensed directly with the compound (II) to give the amine (Ia) in one stage. Production of the isocyanate is then as described previously.

ROUTE B

The aim is to produce isocyanates of formula (Ib)

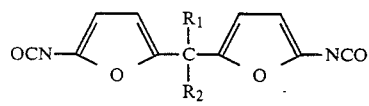
(Ib)

A suitable overall reaction scheme is given below. For the purpose of simplicity, only one furan ring of each difuryl compound (Ib), (IV), (VII) and (VIII) is shown but it should be understood that for these compounds, the other furan ring has the same substituent at the 2-position as that for the ring illustrated.

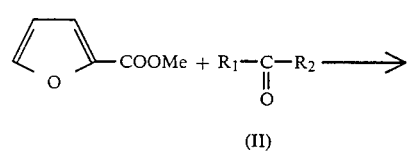
(II)

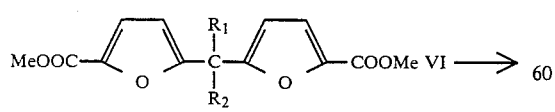

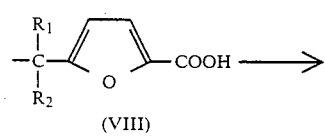
(VIII)

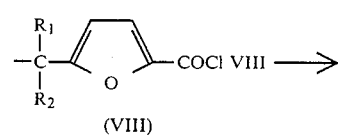
(VIII)

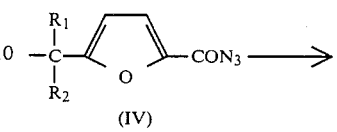
(IV)

(Ib)

The indicated starting material is methyl furoate, which is readily derived from furfural but it should be appreciated that other furoic acid derivatives could be used. Condensation of methyl furoate with (II) may take place under the conditions given for Route A to give diester (VI) which may be converted to diacid (VII) by saponification followed by acidification. Acid (VII) can be converted to diacid chloride (VIII) by conventional routes, e.g. by reaction with excess thionyl chloride followed by removal of residual thionyl chloride under vacuum. Conversion of the diacid chloride (VIII) to diacid azide (IV) can be accomplished by dissolving the diacid chloride (VIII) in acetone and adding an aqueous acetone solution of sodium azide. Reaction to give the diacid azide (IV) occurs over a period of 2-3 hours at 0°-40° C. The diacid azide (IV) may be isolated by extraction and converted to the diisocyanate (Ib) by a Curtius rearrangement, for example by heating (IV) in an inert solvent to leave the crude diisocyanate (Ib).

ROUTE C

The aim is to produce diisocyanate (Ib) and a generalised reaction scheme is shown below. As above certain furan rings are omitted for simplicity.

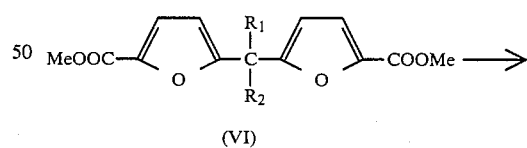
(VI)

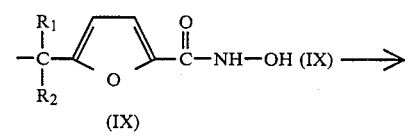
(IX)

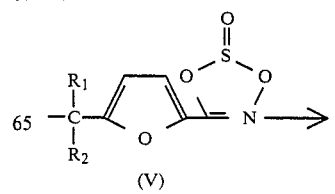
(V)

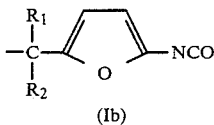

Conversion of diester (VI) (prepared as in Route B) to the bis-hydroxamic acid (IX) may be by reaction with hydroxylamine in methanol. The compound (IX) may be isolated and then reacted with thionyl chloride in ether to give the bis-nitrile sulphite (V). Excess thionyl chloride is removed from the product and the bis-nitrile sulphite (V) heated in an inert solvent until no more $SO_2$ is evolved, so as to yield diisocyanate (Ib).

The invention will be further described by way of example only with reference to the following non-limiting Examples. In the Examples melting points were determined in open capillary tubes and are uncorrected. IR spectra were recorded using a Perkin Elmer model 710B. NMR spectra were obtained using a Perkin Elmer R32 instrument at 90 MHz in carbon tetrachloride solvent and with tetramethylsilane internal standard. Notation used is as follows: For IR spectra, wavenumbers are in $cm^{-1}$, intensities are quoted as: vs (very strong); s (strong); m (medium); or w (weak), and assignments are quoted as oop (out of plane deformation or "wag") def (deformation) and str (stretch). NMR data are given as 5 values in ppm, the multiplicity being represented by: m (multiplet); q (quartet); d (doublet); s (singlet) Coupling constants J, are in Hz (cps). Assignments are quoted in the form; no. of protons (H), and structural origin. Combustion analyses are quoted in absolute percent by weight. Derivatives, where quoted, all had satisfactory combustion analysis and no further data are given other than mps.

EXAMPLE 1

Preparation of bis(5-isocyanato-2-furyl)methane 15 g of the diacid chloride of bis(5-carboxy-2-furyl)methane were dissolved in 80 ml acetone in a flask, equipped with magnetic stirrer and thermometer, and maintained at 0° C. in an ice bath. To this solution was added dropwise, over a period of 30 minutes and keeping the temperature below 5° C., a solution of 14.3 g sodium azide in 80 ml acetone and 60 ml water. The ice bath was then removed and the mixture allowed to attain room temperature over a period of three hours. After this time the mixture consisted of an aqueous and an organic layer and the latter was separated off, extracted with ether and the ether extract washed with cold water until the washings were light in colour. The ether extract was then dried over magnesium sulphate, filtered and rotary-evaporated below 40° C. The residue was the crude diazide, which showed bands in the infra red spectrum (IR) at 2130 and 1690 $cm^{-1}$ (due to the azide group) but no band at 1740 $cm^{-1}$ (due to the carbonyl group) showing the absence of acid chloride.

The crude azide was then dissolved in 100 ml anhydrous toluene and this solution placed in a dropping funnel which was then attached to a 250 ml flask equipped with a nitrogen inlet, thermometer, condenser and bubbler. The flask was charged with 50 ml dry toluene and nitrogen was passed through to purge out air. The nitrogen was then turned off and the flask was warmed to 60° C. The azide solution was gradually added from the funnel over a 30 minute period while the flask continued to be slowly warmed. Nitrogen began to be evolved above ca. 70° C. and this temperature was maintained until the remaining azide had been added. Heating was continued: nitrogen evolution became vigorous between 75° and 90° C. As the rate of nitrogen evolution slowed down, the temperature was raised to reflux until no further bubbles were seen in the bubbler, the total reaction time being about 2 hours. The solution was then cooled and filtered, the red filtrate vacuum stripped and the resultant crude isocyanate distilled in vacuo to yield approx. 3 ml of a straw-yellow liquid with a musty odour. This was bis(5-isocyanato-2-furyl)methane, and had the following properties:

$n_D^{23}$: 1.5448,
Bp: 101°–3°/0.3 mm, mp 17.5°–18° C.
Found: C 57.4; H 2.3; N 12.2%. Calcd. for $C_{11}H_6N_2O_4$: C 57.4; H 2.6; N 12.2%.
IR($cm^{-1}$) 2265, 2240 vs, NCO str; 1583 m, C=C str; 785 s, HC=CH oop; 764 w (uncertain origin). N.B. The last 3 quoted I.R. bonds are typical of 2,5-disubstituted furans.

The liquid darkens on exposure to light and air, and owing to this instability it was not possible to obtain an NMR spectrum.

EXAMPLE 2

Preparation of 1,1-bis(5-isocyanato-2-furyl)ethane

Route B (azide method)

8 g of the diacid chloride of 1,1-bis(5-carboxy-2-furyl)ethane in 50 ml acetone were treated with a solution of 7.25 g sodium azide in 30 ml water and 30 ml acetone, at 5° C. over a period of 15 minutes and the mixture then stirred for 2½ hours during which time the temperature was allowed to rise to ambient. The azide was then separated as in example 1. 8.6 g crude azide was obtained and this was used without further purification for the next stage. However, the azide could be obtained in the pure state as colourless crystals from toluene, mp 93° with decomposition. The IR spectrum of this azide showed bands at 2150 $cm^{-1}$(s) and 1690 $cm^{-1}$(s) due to the azide group.

The crude azide was dissolved in 100 ml dry toluene and converted into the isocyanate as described in Example 1, except that nitrogen began to be evolved above 85° C. Reaction was complete after 2 hours and the mixture was cooled, filtered, evaporated and vacuum distilled to yield the pure isocyanate as a straw-yellow, musty-smelling liquid whose physical data are as follows:

$n_D^{20}$: 1.5395,
Bp: 110°/0.35 mm.
Found: C 58.9; H 2.9; N 11.6%. Calcd. for $C_{12}H_8N_2O_4$: C 59.0; H 3.3; N 11.5%.
IR($cm^{-1}$) 2250 vs, NCO str; 1579 m, C=C str; 782 s, HC=CH oop; 747 w (uncertain origin) (see note in Example 1)

This liquid also darkened on exposure to light and air.

EXAMPLE 3

Preparation of 1,1-bis(5-isocyanato-2-furyl)ethane

Route C (nitrile sulphite method)

The bis-hydroxamic acid of 1,1-bis(5-carboxy-2-furyl)ethane was first prepared as follows. A solution of hydroxylamine was prepared by mixing 7 g sodium methoxide, 95 ml methanol and 9.0 g hydroxylamine hydrochloride. 15 g of 1,1-bis(5-carbomethoxy-2-furyl)ethane were then added along with a further 5.83 g sodium methoxide in 25 ml methanol, the mixture shaken for 8 hours then allowed to stand overnight. The mixture was then just acidified (to litmus) with concd. hydrochloric acid and filtered. The material retained by the filter was washed with water to remove mineral salts and acid: the filtrate was evaporated and the residue washed with water. The washed products were combined and oven-dried to yield 13 g (86%) of the bis-hydroxamic acid as a white powder. This could be further purified by crystallisation from DMF/chloroform to yield a powder, mp 186° (decomposes abruptly).

Found: C 51.5; H 4.6; N 10.0% Calcd. for $C_{12}H_{12}N_2O_6$: C 51.4; H 4.3; N 10.0%.

8 g of this product were dispersed in 100 ml dry diethyl ether in a flask equipped with a stirrer, double-surface condenser and 50 ml dropping funnel. 7.5 g thionyl chloride was then added at room temperature and when addition was complete (20 minutes) the temperature was raised to reflux and maintained there for 3 hours. The mixture as then cooled and filtered to give a dark residue and a reddish-brown filtrate. The filtrate was vacuum stripped to give 5.4 g of a dark liquid which was the crude bis(nitrile sulphite). This was dissolved in 50 ml dry toluene and the solution warmed to 100° C.: bubbles of sulphur dioxide began to be evolved above 80° C. After 1½ hours, no further bubbles could be seen and the liquid was cooled, filtered and the filtrate evaporated to yield a few ml of the crude diisocyanate, which was shown by IR spectra to be essentially identical to the product from Example 2.

EXAMPLE 4

Preparation of 1,1-bis(5-aminomethyl-2-furyl)ethane (Amine "A")

N-furfuryl formamide (NFF) was first prepared by refluxing together furfurylamine, formic acid and heptane, and distilling off the water azeotrope and excess formic acid. The NFF was purified by fractional distillation, bp 116°–7°/0.05 mm. Yield 93.8%, $n_D^{20}$ 1.5032, $d^{20}$ 1.178.

100 g NFF were mixed with 280 ml of 40% orthophosphoric acid in a 1 l flask immersed in an ice/salt bath at −7° C., and 23.3 g (30 ml) acetaldehyde added dropwise with stirring. The mixture changed through colourless to lime green, green-orange then amber, and the temperature rose to 3° C. Reaction was continued for 45 minutes at 0° C., then the mixture was neutralised by adding a solution of 25% sodium hydroxide, and extracted with a total of 200 ml chloroform. The extract was washed, dried, filtered and evaporated to yield 110.5 g of an orange oil. This was crude 1,1-bis(5-formamidomethyl-2-furyl)ethane, which could be obtained in a pure form, by crystallisation from ethanol/petroleum ether, with mp 75°–6° C.

The crude product was hydrolysed under reflux using 75 g potassium hydroxide in a mixture of water (100 ml) and methanol (100 ml) for 3 hours. The crude amine was isolated as a brown liquid in 98.7% yield after distilling off the methanol and extracting the residue with chloroform, followed by evaporation. This product was distilled in vacuo to furnish the pure diamine "A" in overal yield of 65% (based on NFF) as a viscous, pale yellow liquid whose physical properties are:

$n_D^{20}$: 1.5421,

Bp: 124°-5°/0.04 mm; bis-acetamide mp 92°-2°

Found: C 65.4; H 7.5; N 12.6%. Calcd. for $C_{12}H_{16}N_2O_2$=C 65.4; H 7.3; N 12.7%.

IR spectrum (cm$^{-1}$): 3350 m, 3280 m, N—H str; 1610 m, N—H def; 1558 s, C=C str; 787 s HC=CH oop; 749 w (uncertain origin)

N.B. The last three quoted IR bands are characteristic of 2,5-disubstituted furfuryl types.

NMR(δ): 5.85 m, 4H in 3- and 4-furan; 4.05 q, J=7 Hz, 1H in H—C—CH$_3$; 3.63s, 4H in CH$_2$; 1.5d, J=7 Hz, 3H in CH$_3$; 1.2s, 4H in NH$_2$.

The bis-hydrochloride of Amine "A" was prepared in the usual way, by adding 19 g concd hydrochloric acid to 20 g of the diamine dissolved in 35 ml methanol and keeping the temperature below 10° C., then pouring into acetone (200 ml) filtering, washing with acetone and drying in vacuo. Yield 25.4 g, 94%.

EXAMPLE 5

Preparation of 1,1-bis(5-isocyanatomethyl-2-furyl)ethane (Isocyanate "A")

10 g of the dried bis-hydrochloride of Amine "A" were finely ground and dispersed in 150 ml dry chlorobenzene in a 500 ml reaction vessel equipped with a gas inlet tube, stirrer, condenser and thermometer. The flask and its contents were cooled to 0° C. and gaseous chlorine-free phosgene passed in slowly, with stirring for 1½ hours after which time approx. 15 g phosgene had been absorbed. The temperature of the reaction mixture was gradually raised while continuing to pass phosgene in at a rate of ca. 15 g per hour: since most of the phosgene was not absorbed in the reaction mixture the excess was destroyed by passing through alkali traps. Hydrogen chloride began to be evolved above 90° to 100° C.; reaction was continued for a total of 10 hours at 120° C. then phosgene addition was stopped and nitrogen passed through while cooling to room temperature. The resultant dark solution was then filtered and the chlorobenzene removed on a rotary film evaporator. The residue, a dark liquid, was distilled in vacuo to yield 6 g (65% yield) of isocyanate "A" as a liquid with a faint odour and the following physical properties:

$n_D^{20}$: 1.5186

Bp: 143.5°/0.2 mm

Found: C 62.0; H 4.5; N 10.2%; Calcd. for $C_{14}H_{12}N_2O_4$=C 61.8; H 4.4; N 10.3%.

IR (cm$^{-1}$) 2230 vs NCO str; 1555 m C=C str; 792 HC=CH oop; 758 m (see note for Example 4)

NMR (δ): 6.15 d, J=3 Hz, 2H in 3-furan; 6.00d, J=3 Hz, 2H in 4-furan; 4.3 s, 4H in CH$_2$; 4.2(q), J=7 Hz, 1H in H—C—CH$_3$; 1.6d, J=7 Hz, 3H in CH$_3$.

EXAMPLE 6

Preparation of 2,2-bis(5-aminomethyl-2-furyl)propane (Amine "B")

27.8 g acetone were added slowly, with stirring, to a solution of 100 g NFF in 90 ml concd. hydrochloric acid at 0° C. and the mixture was then allowed to exotherm over a period of 2 hours, to 40° at which temperature it was maintained for a further hour then cooled and neutralised with sodium hydroxide solution. The product was extracted with chloroform, washed and rotary evaporated to yield 104 g of a viscous, amber oil which was the crude formamido-derivative of Amine "B".

100 g of this product were hydrolysed by refluxing for 6 hours with a solution of 60 g sodium hydroxide in 60 ml water and 80 ml methanol. The resultant brown oil, crude Amine "B", was recovered as in Example 4 to give 80 g crude product and on vacuum distillation this gave 47 g pure diamine as a viscous, colourless liquid whose physical properties are:

$n_D^{20}$: 1.5364

Bp: 138°/0.1 mm, mp 25°–7° C. Bis-acetamide, mp 136.5°–7.5° C.

Found: C 66.7; H 7.8; N 11.7%. Calcd for $C_{13}H_{18}N_2O_2$=C 66.6; H 7.7; N 12.0%.

IR (cm$^{-1}$) 3360 m, 3275 m N—H str; 1610 N—H def; 1550s C=C str; 792s HC=CH oop; 743 w (uncertain origin) (see note for Example 4).

NMR (δ): 5.92 d, J=3 Hz and 5.82 d, J=3 Hz, 4H in 3- and 4-furan; 3.65s, 4H in CH$_2$; 1.57s, 6H in CH$_3$; 1.2s, 4H in NH$_2$.

The bis-hydrochloride of amine B was prepared by following the procedure of Example 4.

EXAMPLE 7

Preparation of 2,2-bis(5-isocyanatomethyl-2-furyl)propane (Isocyanate "B")

10 g of the bis-hydrochloride of Amine "B" were finely ground and dried then dispersed in 150 ml anhydrous chlorobenzene. An excess of phosgene over that required by stoichiometry was passed into the stirred suspension at 0° to 3° C. The mixture was heated while continuing phosgene addition at a rate of approx. 15 g per hour. The reaction was continued over 3 days, during which heating was applied for a total of 15 hours. Reaction was shut down each night and excess phosgene passed into the mixture the following morning before resuming heating. When essentially all the hydrochloride had dissolved and hydrogen chloride was no longer being evolved, the dark amber mixture was cooled to room temperature, purged with nitrogen, filtered and the chlorobenzene removed using a rotary film evaporator. The residue was distilled in vacuo to yield 6.5 g (69.7%) of isocyanate "B", as a faintly yellow liquid with very little odour. Its physical properties were found to be:

$n_D^{20}$: 1.5132

Bp: 124°/0.04 mm

Found: C 62.9; H 4.6; N 9.9%. Calcd. for $C_{15}H_{14}N_2O_4$=C 62.9; H 4.9; N 9.8%.

IR (cm$^{-1}$) 2225 vs, NCO str; 1547m C=C str; 786s HC=CH oop; 750 m (uncertain origin) (see note for Example 4) NMR (δ): 6.12d, J=3 Hz, 2H in 3-furan; 5.95 d, J=3 Hz 2H in 4-furan; 4.27 s, 4H in CH$_2$; 1.63 s, 6H in CH$_3$.

Both this compound and isocyanate "A" are sufficiently stable to be stored, essentially unchanged for many weeks at room temperature (preferably in a dry atmosphere).

EXAMPLE 8

A polyurethane elastomer was prepared from isocyanate "A" by reacting 1.36 g of the isocyanate with 2.30 g of an oxypropylated. 1,2,6-hexanetriol-based polyol of molecular weight 690, stirring and pouring into a flat mould then curing at 80° C. for 3 hours. The resultant polymer was a clear, orange rubber. The glass transition temperature (T$_g$) of this polymer was measured to be −8° C. by Differential Thermal Analysis (DTA) using a heating rate of 20° C./min on a DuPont 990 instrument.

EXAMPLE 9

A simple polyurethane network was prepared using 1.99 g isocyanate "B" mixed with 3.26 g of the same triol referred to in Example 8. The material was cured for 4 hours at 80° C., gelation occurring after approx. 1 hour. The resultant elastomer was clear and slightly yellow, and had a T$_g$ of −9° C. (conditions as in Example 8) as measured by DTA.

We claim:

1. Compounds of the formula (I)

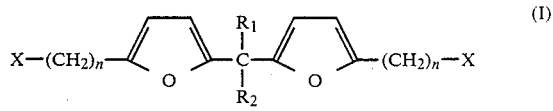

in which R$_1$ and R$_2$ are the same or different and are selected from the group consisting of hydrogen, unsubstituted ethyl radicals, methyl radicals, vinyl radicals, halogen substituted vinyl radicals, halogen substituted methyl radicals and halogen substituted ethyl radicals, X is a —NH$_2$ or —NCO group, and n is 0 or 1 with the proviso that n is not 0 when X is —NH$_2$.

2. Compounds as claimed in claim 1, wherein at least R$_1$ or R$_2$ is a trichloromethyl group.

3. A compound as claimed in claim 1 and which is bis(5-isocyanato-2-furyl)methane.

4. A compound as claimed in claim 1 and which is 1,1-bis(5-isocyanato-2-furyl)ethane.

5. A compound as claimed in claim 1 and which is bis(5-isocyanatomethyl-2-furyl)methane.

6. A compound as claimed in claim 1 and which is 1,1-bis(5-isocyanatomethyl-2-furyl)ethane.

7. A compound as claimed in claim 1 and which is 2,2-bis(5-isocyanatomethyl-2-furyl)propane.

8. A compound as claimed in claim 1 and which is bis(5-aminomethyl-2-furyl)methane.

9. A compound as claimed in claim 1 and which is 1,1-bis(5-aminomethyl-2-furyl)ethane.

10. A compound as claimed in claim 1 and which is 2,2-bis(5-aminomethyl-2-furyl)propane.

* * * * *